US00PP25637P3

(12) United States Plant Patent
Tufaro

(10) Patent No.: US PP25,637 P3
(45) Date of Patent: Jun. 23, 2015

(54) STRAWBERRY PLANT NAMED 'MARISOL'

(50) Latin Name: ***Fragaria×ananassa* Duchesne**
Varietal Denomination: Marisol

(71) Applicant: SOCIEDAD NOVA SIRI GENETICS s.n.c. di TUFARO NICOLA & C., Nova Siri (MT) (IT)

(72) Inventor: Nicola Tufaro, Nova Siri (IT)

(73) Assignee: NOVA SIRI GENETICS S.R.L., Nova Siri (MT) (IT)

( * ) Notice: Subject to any disclaimer, the term of this patent is extended or adjusted under 35 U.S.C. 154(b) by 196 days.

(21) Appl. No.: 13/987,139

(22) Filed: Jul. 3, 2013

(65) Prior Publication Data

US 2014/0020143 P1 Jan. 16, 2014

(30) Foreign Application Priority Data

Jul. 10, 2012 (QZ) ..... PBR 2012/1377

(51) Int. Cl.
*A01H 5/00* (2006.01)
*A01H 5/08* (2006.01)

(52) U.S. Cl.
CPC ..... *A01H 5/0893* (2013.01)
USPC ..... Plt./208

(58) Field of Classification Search
USPC ..... Plt./208
See application file for complete search history.

*Primary Examiner* — Annette Para
(74) *Attorney, Agent, or Firm* — Buchanan, Ingersoll & Rooney P.C.

(57) ABSTRACT

A new and distinct short-day strawberry cultivar is provided. Attractive semi-early ripening bright red primarily conical fruit having a firm flesh is formed in good yields. Additionally, some fruit having a forked tip commonly is produced in a lesser yield. White inflorescence is formed on a semi-early basis that commonly is disposed slightly above the foliage. A calyx commonly is displayed having a diameter when open that is generally smaller than the diameter of the open corolla. A dense upright generally globose growth habit is displayed.

6 Drawing Sheets

Botanical/commercial classification: *Fragaria×ananassa* Duchesne/Strawberry Plant.

Varietal denomination: cv. Marisol.

BACKGROUND OF THE INVENTION

The new and distinct short-day strawberry cultivar of the present invention was the product of a controlled breeding program that was carried out at Nova Siri (MT) Italy located at 40° 08' 40" N.-16° 39' 40" E. and 10 meters above sea level. The female parent (i.e., the seed parent) was the 'Siris' cultivar (non-patented in the United States and EU No. 34843) and the male parent (i.e., pollen parent) was the 'Milsei' cultivar (U.S. Plant Pat. No. 7,864). The parentage of the new cultivar can be summarized as follows:

'Siris'×'Milsei'.

The seeds resulting from the pollination were sown and small plants were obtained which were physically different from each other. Selective study and testing resulted in the identification of a single plant of the new cultivar.

The new cultivar initially was designated AD.08.069.

It was found that the new short-day strawberry cultivar of the present invention displays the following combination of characteristics:

(a) exhibits a dense, upright generally globose growth habit, (b) displays on a semi-early basis white inflorescence at a level slightly above the foliage, (c) commonly displays a calyx diameter that generally is smaller than the diameter of the corolla when open, and (d) forms in abundance semi-early ripening large bright red primarily conical fruit having a firm flesh that is longer than broad in configuration as well as some fruit having forking at the tip.

The new cultivar of the present invention can be readily distinguished from previously known strawberry cultivars including the 'Sabrosa' cultivar (U.S. Plant Pat. No. 16,558) as indicated in detail hereafter.

The new cultivar possesses characteristics that commonly are sought by commercial strawberry growers. Substantially uniform firm bright red semi-early ripening fruit is provided in good yields. Accordingly, the new cultivar is considered to be a promising new plant introduction.

The new cultivar has been asexually reproduced by the use of stolons at Ochla, Poland located at 51° 848 N.-15° 447 E. and by in vitro tissue culture. No rooting problems were encountered. The combination of characteristics exhibited by the new plant has been found to be stable and is reliably transmitted to succeeding generations following such asexual reproduction. Accordingly, the new cultivar reproduces true-to-type manner by such asexual reproduction.

The new plant has been named 'Marisol'.

BRIEF DESCRIPTION OF THE PHOTOGRAPHS

The accompanying photographs show, as nearly true as it is reasonably possible to make the same in color illustrations of this character, typical specimens of the new cultivar as well as typical specimens of the 'Sabosa' cultivar (U.S. Plant Pat. No. 16,558) for comparative purposes. The plants had been asexually reproduced from stolons and were planted under the cover of plastic tunnels during mid-October 2012 at Nova Siri (MT), Italy.

Figure 1:
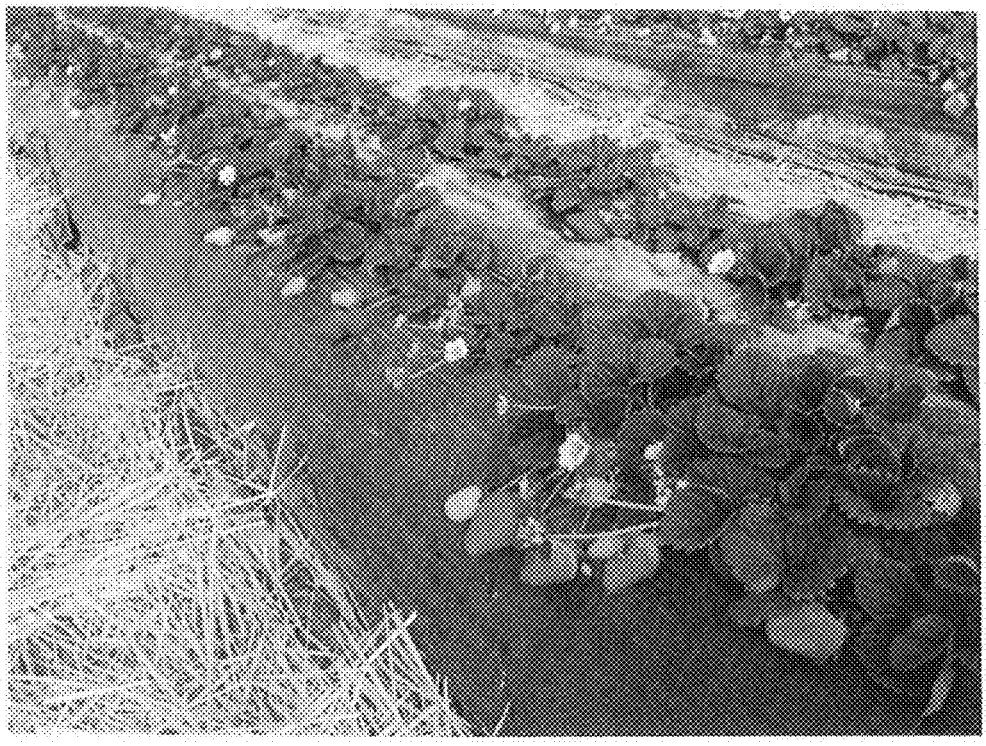
FIG. 1 shows rows of flowering and fruiting young plants of the new cultivar on Feb. 25, 2013 where the flowers commonly are disposed slightly above the foliage.
Figure 2:
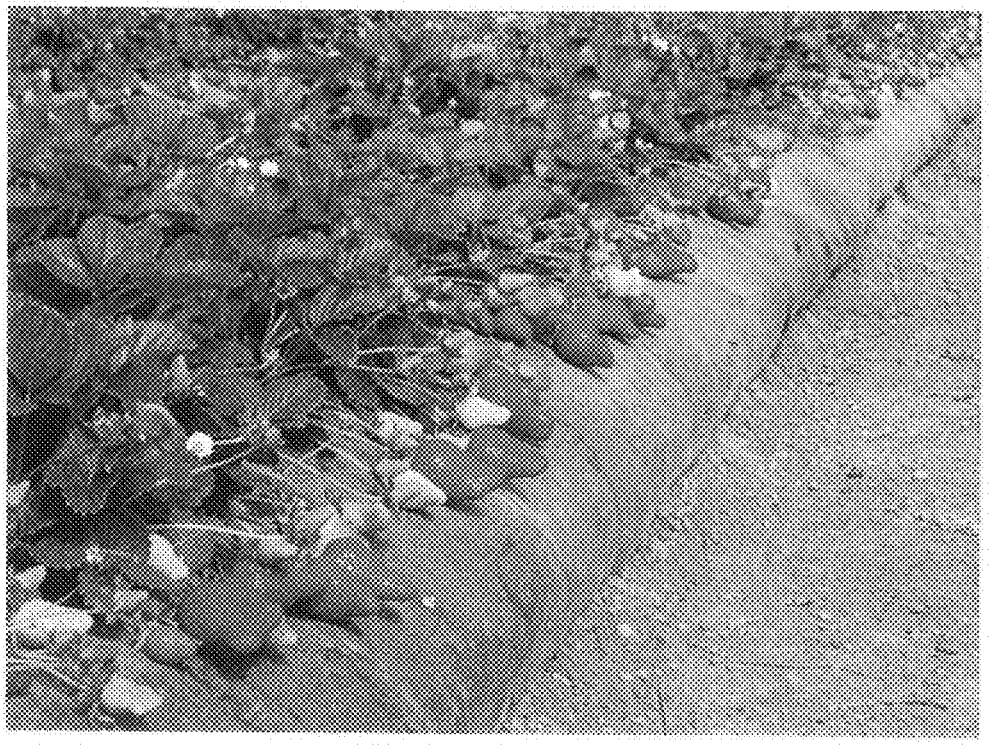
FIG. 2 shows fruiting plants of the new cultivar on Mar. 25, 2013 wherein abundant fruit production is apparent.
Figure 3:
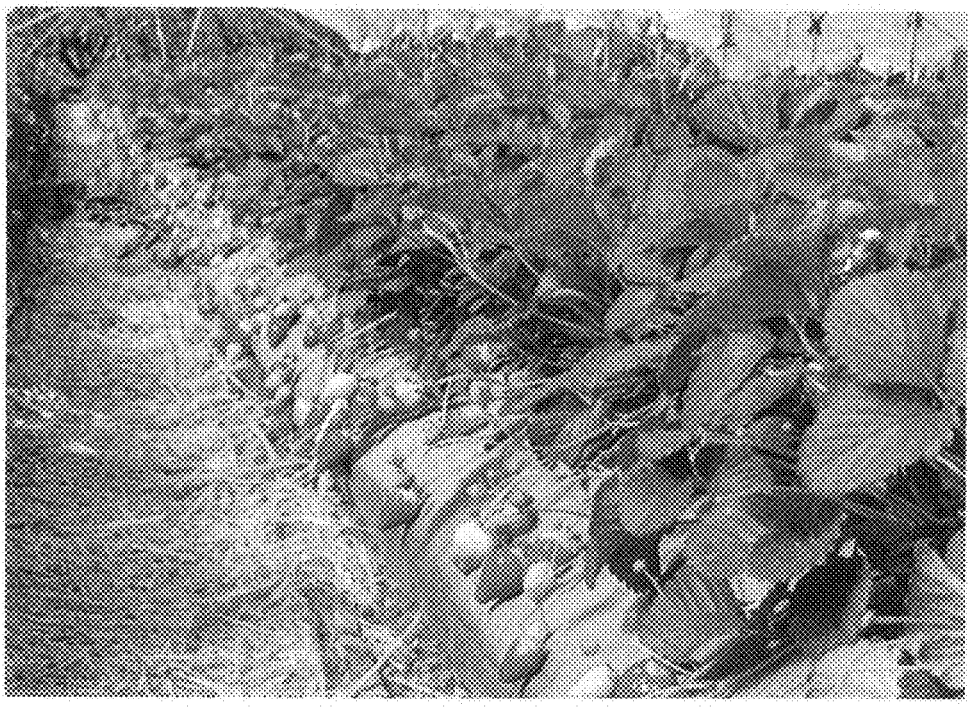
FIG. 3 shows more mature fruiting plants of the new cultivar on May 10, 2013 where the plant density is further illustrated.
Figure 4:
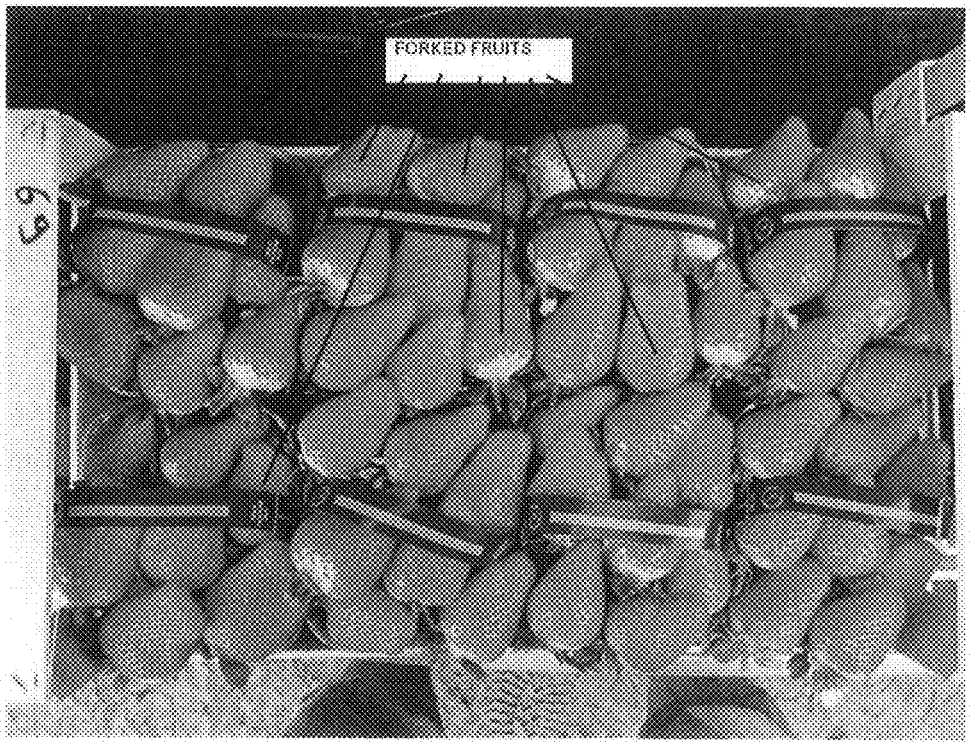

FIG. 4 shows a crate of the fruit of the new cultivar. The overall fruit shape and coloration is apparent. Approximately 90 percent of the fruit is conical in configuration and approximately 10 percent of the fruit is more cylindrical in configuration with some forking at the tip.

Figure 5:
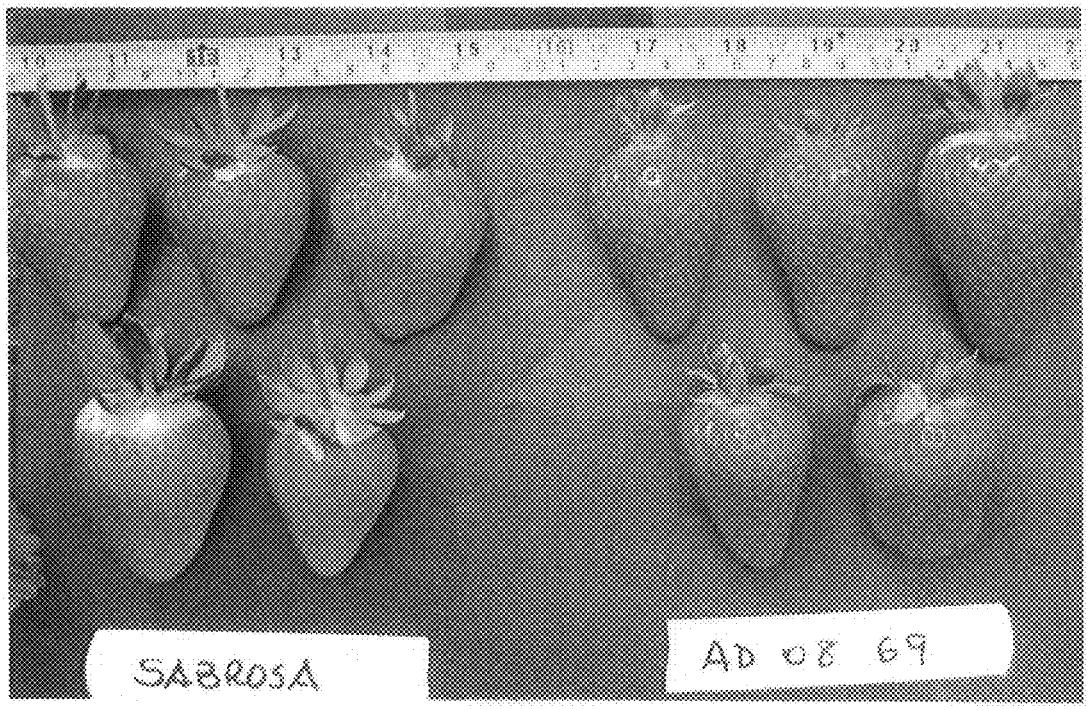

FIG. 5 shows a close view of typical attractive fruit of the new cultivar (right) and of the 'Sabrosa' cultivar (left). The 'Marisol' fruit is somewhat larger. The length:width ratio is larger, the fruit coloration is slightly darker, and more even over the entire surface for the 'Marisol' cultivar. Additionally, the disposition of the sepals of the calyx is generally more upwards for the 'Marisol' cultivar and more outwards for the 'Sabrosa' cultivar. Measurement in centimeters and in inches is included for comparative purposes.

Figure 6:
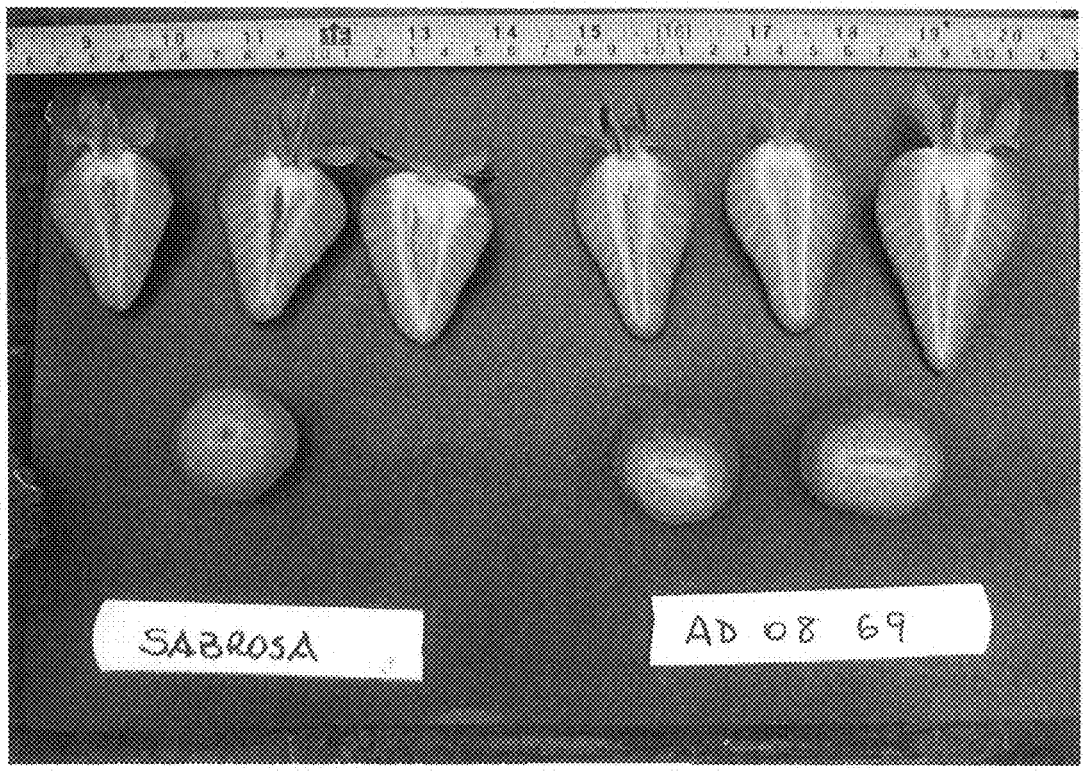

FIG. 6 shows close internal views of typical fruit of the 'Marisol' cultivar (right) and the 'Sabrosa' cultivar (left). An internal fruit cavity is largely absent in the 'Marisol' cultivar fruit and is present in the 'Sabrosa' cultivar fruit. Measurement in centimeters and in inches is included for comparative purposes.

Figure 7:
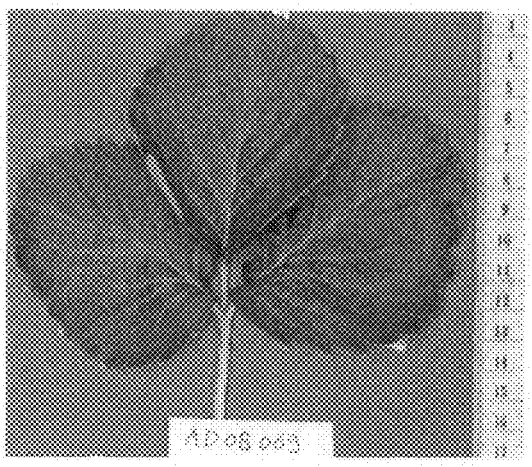

FIG. 7 shows the typical upper (i.e., adaxial) surface of a three-leaflet leaf of the 'Marisol' cultivar. The terminal leaflet unlike that of the 'Sabrosa' cultivar tends to be longer than broad. Dimensions in centimeters are included for comparative purposes.

Figure 8:
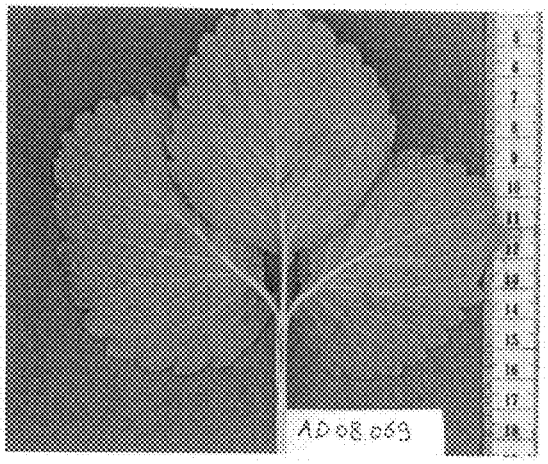

FIG. 8 shows the typical under (i.e., abaxial) surface of a three-leaflet leaf of the 'Marisol' cultivar. Dimensions in centimeters are included for comparative purposes.

Figure 9:
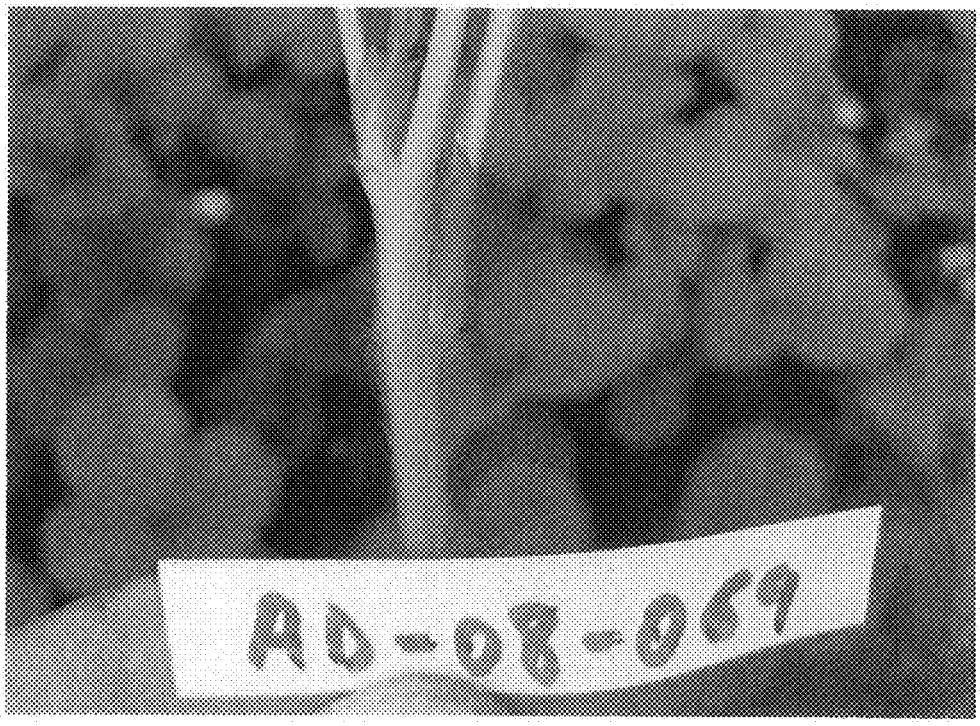

FIG. 9 shows a typical pedicel of the 'Marisol' cultivar wherein pubescence on the surface is generally disposed upwardly.

Figure 10:
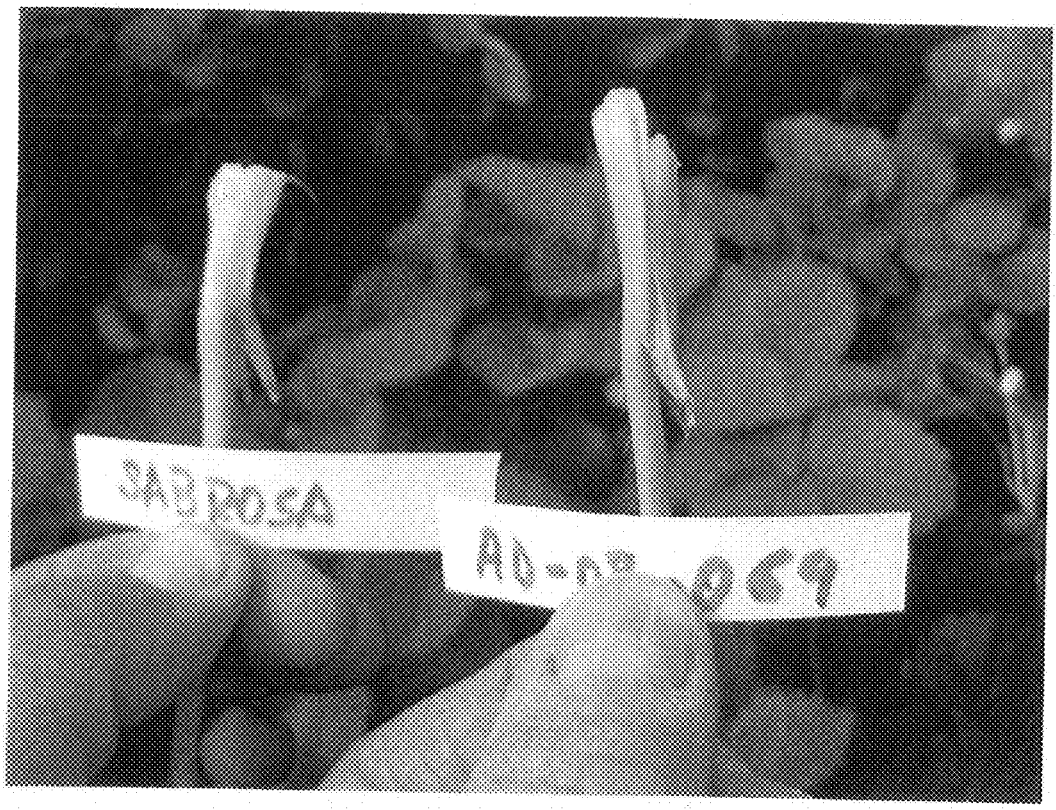

FIG. 10 illustrates at the right a typical stipule of the 'Marisol' cultivar and at the left a typical stipule of the 'Sabrosa' cultivar. The stipule of the 'Marisol' cultivar tends to be larger than that of the 'Sabrosa' cultivar and to bear some anthocyanin coloration unlike that of the 'Sabrosa' cultivar.

Figure 11:
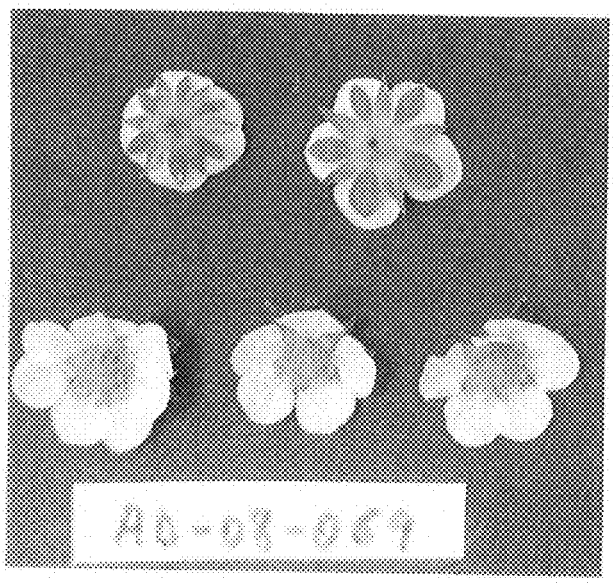

FIG. 11 illustrates reverse (top) and obverse (bottom) views of typical inflorescence of the 'Marisol' cultivar. The open calyx diameter tends generally to be smaller than that of the open corolla.

Figure 12:
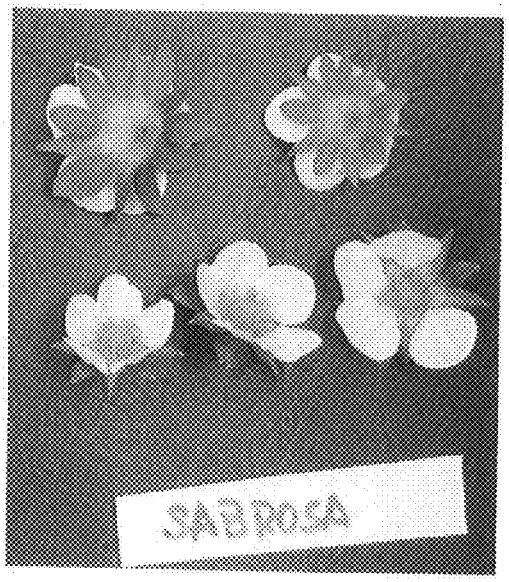

FIG. 12 illustrates for comparative purposes reverse (top) and obverse (top) views of typical inflorescence of the 'Sabrosa' cultivar. The open calyx diameter tends to be somewhat larger than that of the open corolla.

Figure 13:
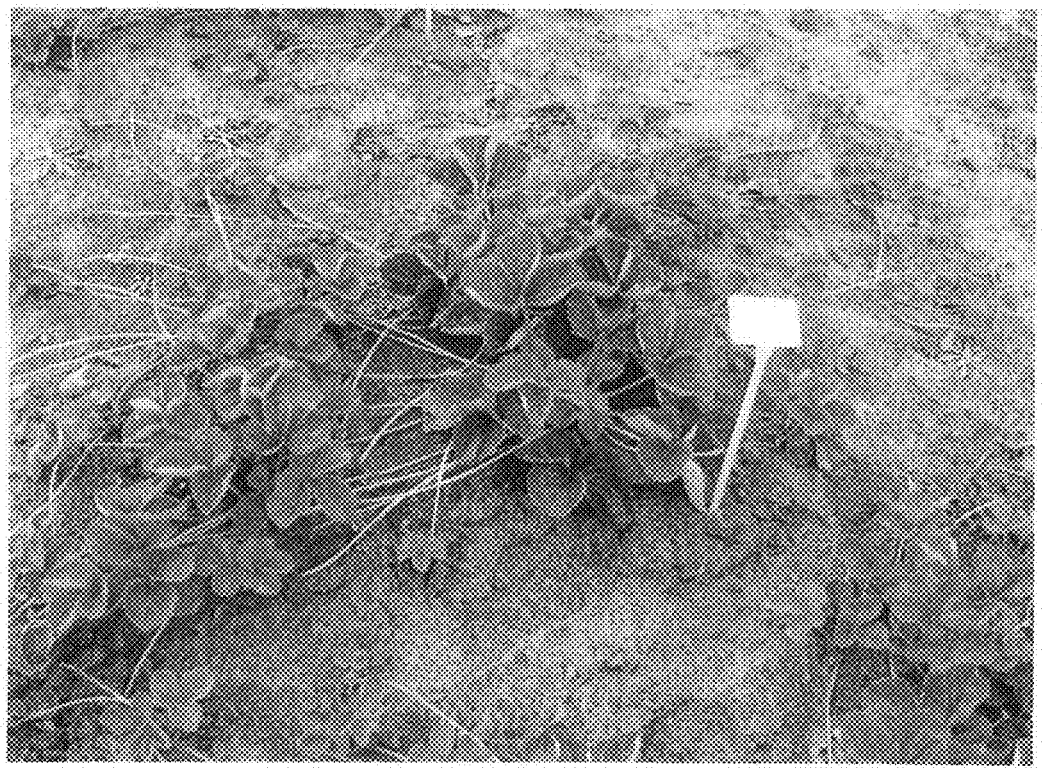

FIG. 13 illustrates typical tendency of the 'Marisol' cultivar to form stolons in a medium to high frequency with medium anthocyanin coloration being present on the stolons.

Figure 14:
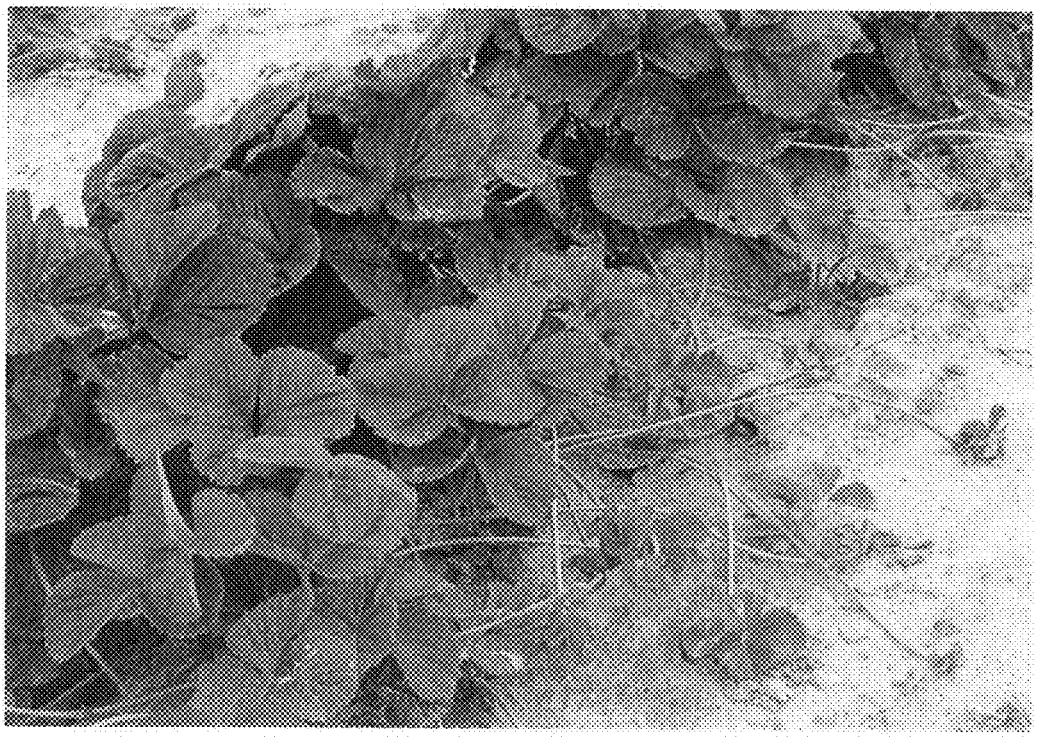

FIG. 14 illustrates for comparative purposes typical stolon formation exhibited by the 'Sabrosa' cultivar with the substantial absence of anthocyanin coloration.

DETAILED BOTANICAL DESCRIPTION

The described plants had been asexually reproduced by the use of stolons and were growing under the cover of plastic tunnels at Nova Siri (MT) Italy. The chart used in the identification of color is The R.H.S. Colour Chart (1995 Edition or equivalent) of The Royal Horticultural Society, London, England. Reference to common color terms is to be accorded ordinary dictionary significance.

Botanical class: *Fragaria×ananassa,* Duchesne, cv. 'Marisol'.

Plant:

*Type.*—Short-day.

*Configuration.*—Upright, relatively dense, and generally globose.

*Vigor.*—Medium strong.

*Height.*—Commonly approximately 28 to 30 cm on average.

*Width.*—Commonly approximately 30 on average.

*Leaflets.*—Three in number, medium in size, commonly up to approximately 9 cm in length on average and up to approximately 8 cm in width on average; the terminal leaflet commonly is moderately longer in length than width and commonly is approximately 8 cm in length on average and approximately 7.3 cm in width on average, possess a concave cross section, a serrate to crenate margin, and a rounded base; blistering commonly is medium; the glossiness on the upper surface is medium; the upper surface coloration commonly is near Green Group 140A to Green Group 141B and the under surface coloration commonly is near Green Group 139C to Green Group 141C.

*Stolons.*—Medium to high in quantity, commonly approximately 55 cm in length on average, medium density of pubescence, near Green Group 142A to 142B in coloration, commonly with medium intensity anthocyanin coloration of near Red-Purple Group 65B to 65C as illustrated in FIG. 13. Stolons commonly are produced somewhat more numerously than the 'Sabrosa' cultivar with anthocyanin coloration commonly being absent on the stolons of the 'Sabrosa' cultivar.

*Petioles.*—Commonly approximately 19 to 24 cm in length on average, near Green Group 142A to 142B in coloration, and commonly bear horizontally disposed fine pubescence.

*Stipules.*—Larger than those of the 'Sabrosa' cultivar as illustrated in FIG. 10, near Yellow-Green Group 145B to Yellow-Green Group 149C in coloration, and commonly bear some anthocyanin coloration of near Red-Purple Group 65B to 65C unlike the stipules of the 'Sabrosa' cultivar where anthocyanin coloration was not observed.

Inflorescence:

*Flowering time.*—Semi-early.

*Flower number.*—Medium, commonly 5 or 6.

*Pedicel hairs.*—Pubescence generally disposed upwards.

*Size.*—Large, with primary flowers commonly being approximately 2.5 to 3.2 cm in diameter on average, and secondary flowers commonly being approximately 2.5 cm in diameter on average.

*Petals.*—Overlapping, nearly round in configuration, commonly number approximately 5 to 8 on average, normally 6 in number, commonly moderately greater in width than length, commonly approximately 8.5 mm in length on average and approximately 9 mm in width average, and near White Group 155B to 155C in coloration.

*Anthers.*—Commonly number approximately 22 to 25 on average and disposed above the stamens. Yellow pollen is formed in abundance as illustrated in FIG. 11. The plant is self-fertile.

*Sepals.*—Generally lanceolate in configuration, commonly are generally disposed upwards as illustrated in FIG. 5, commonly number approximately 10 to 13 on average which can be compared to approximately 10 to 12 for the 'Sabrosa' cultivar, commonly approximately 5 to 7 mm in length on average and approximately 2 to 3 mm in width on average at the broadest point, unlike the 'Sabrosa' cultivar the diameter of the open calyx commonly generally is less than that of the corolla (as illustrated in FIG. 11), and commonly the coloration is near Green Group 143A on the upper surface and near Green Group 142A to 142B on the under surface.

Fruit:

*Bearing.*—Non-remontant.

*Timing.*—Semi-early fruiting, commonly with approximately 30 to 35 days from first blooming to first fruit ripening. This can be compared to approximately 35 to 40 days between first blooming and first fruit ripening for the 'Sabrosa' cultivar.

*Shape.*—Primarily conical in configuration with a minor quantity of fruits bearing a more cylindrical configuration with forking at the tip as illustrated in FIG. 4. There commonly is only a slight shape difference between terminal and other fruit.

*Size.*—Large, with the primary fruit commonly being approximately 5 to 5.5 cm in length and approximately 4 to 5.2 cm width at the broadest point. The length:width ratio commonly is greater than that of the 'Sabrosa' cultivar.

*Surface.*—Commonly with slight unevenness and strong glossiness.

*External color.*—Substantially uniform and commonly bright medium red, near Red Group 42B to 42C, and slightly darker than that of the 'Sabrosa' cultivar.

*Internal color.*—Medium red, and commonly near Red Group 40A to 40B, with a lighter red core of near Red Group 40B.

*Firmness.*—Good, with medium flesh firmness, and commonly with somewhat more firmness than the 'Sabrosa' cultivar.

*Cavity.*—Very small or absent fruit cavity (as illustrated in FIG. 6).

*Achenes.*—Located below the fruit surface commonly with only a narrow band of 4 to 6 mm where achenes are absent, and commonly near Orange-Red Group 33B to 33C in coloration.

*Calyx.*—The sepals of the calyx commonly tend to be generally disposed upwards as illustrated in FIG. 5 with weak adherence to the fruit.

*Peduncle.*—Approximately 10 to 17 cm in length on average for primary fruit and approximately 11 to 14 cm in length on average for secondary fruit, and commonly near Yellow-Green Group 149A to 149B in coloration.

*Pedicel.*—Commonly near Green Group 142A with pubescence disposed upwards.

SUPPLEMENTAL COMPARATIVE DATA

Hereafter, comparative fruit data is provided for the new 'Marisol' cultivar and the 'Sabrosa' cultivar. On Oct. 15, 2012 plots of fifty (50) plants of each cultivar were planted in four (4) replications at Nova Siri (MT), Italy. The plants had been asexually reproduced by the use of stolons and were growing under the cover of plastic tunnels. The fruit was evaluated and compared during 2013 on the dates indicated. Average data is presented.

Accumulated Production of First Quality Fruit (g/plant)

| Cultivar | February 30th | March 30th | April 30th | May 30th |
|---|---|---|---|---|
| 'Marisol' | none | 51 | 421 | 751 |
| 'Sabrosa' | none | 73 | 270 | 589 |

Average Fruit Weight on Specified Dates

| | March 30th | | April 30th | | May 30th | |
|---|---|---|---|---|---|---|
| Cultivar | First Quality (grams) | Second Quality (grams) | First Quality (grams) | Second Quality (grams) | First Quality (grams) | Second Quality (grams) |
| 'Marisol' | 36.47 | 29.03 | 36.01 | 22.84 | 22.23 | 11.04 |
| 'Sabrosa' | 25.20 | 16.00 | 29.50 | 17.50 | 21.33 | 11.07 |

Comparison of Accumulated Fruit Production May 30th

| Cultivar | First Quality (grams) | Second Quality (grams) | Total (grams) | Percent Second Quality |
|---|---|---|---|---|
| 'Marisol' | 751 | 162 | 913 | 17.74% |
| 'Sabrosa' | 589 | 92 | 681 | 13.50% |

Overall Comparison of Fruit Weight

| Cultivar | g/fruit |
|---|---|
| 'Marisol' | 25.50 |
| 'Sabrosa' | 22.50 |

Fruit Analysis

| | 'Marisol' | 'Sabrosa' |
|---|---|---|
| Firmness (average)* | 0.66 | 0.63 |
| Dry Matter (%)** | 7.70 | 7.50 |
| pH (to 20°) | 3.80 | 3.50 |
| Acidity as Anhydride Citric (%) | 0.75 | 0.75 |
| Soluble Solids (% Brix) | 7.95 | 8.66 |
| Maturity Index | 10.60 | 11.54 |

*Resistance to penetration measured in kilograms using a Turoni (Italy) pentrometer (20 Kg × 0.01).
**Weight of residue from the titration of the fruit after drying at 103° C. until a constant weight is achieved.

Plants of the new 'Marisol' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct short-day strawberry plant that exhibits the following combination of characteristics:

(a) exhibits a dense, upright, generally globose growth habit, (b) displays on a semi-early basis white inflorescence at a level slightly above the foliage, (c) commonly displays a calyx diameter that generally is smaller than the diameter of the corolla when open, and (d) forms in abundance semi-early ripening bright red primarily conical fruit having firm flesh that is longer than broad in configuration as well as some fruit having forking at the tip;

substantially as illustrated and described.

* * * * *